US00PP24760P2

(12) United States Plant Patent
Falstad, III

(10) Patent No.: US PP24,760 P2
(45) Date of Patent: Aug. 12, 2014

(54) *HIBISCUS* PLANT NAMED 'HEARTTHROB'

(50) Latin Name: ***Hibiscus* hybrid (L.)**
Varietal Denomination: Heartthrob

(71) Applicant: Clarence H. Falstad, III, Holland, MI (US)

(72) Inventor: Clarence H. Falstad, III, Holland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 64 days.

(21) Appl. No.: 13/815,748

(22) Filed: Mar. 16, 2013

(51) Int. Cl.
*A01H 5/00* (2006.01)

(52) U.S. Cl.
USPC ..... Plt./257

(58) Field of Classification Search
USPC ..... Plt./257
See application file for complete search history.

(56) References Cited

PUBLICATIONS

Walters Gardens, Inc. (retrieved from the internet at <http://www.waltersgardens.com/plants/General-Perennial/2244_HibiscusHeartthrobPPAF.aspx> 2 pages.*
Susan M. Martin, Walters Garden, Inc. Wholesale Catalog, Jun. 15, 2012, front cover, Summer 2012-Spring 2013, Walters Gardens, Inc., Zeeland, Michigan, USA.
Susan M. Martin, Walters Garden, Inc. Wholesale Catalog, Jun. 15, 2012, p. 122, Summer 2012-Spring 2013, Walters Gardens, Inc., Zeeland, Michigan, USA.

* cited by examiner

*Primary Examiner* — June Hwu
*Assistant Examiner* — Keith Robinson

(57) ABSTRACT

A new and distinct cultivar of hardy herbaceous *Hibiscus* hybrid plant named 'Heartthrob' with mostly upright branched stems bearing broadly ovate-shaped dark green foliage and many large flat-faced, dark, greyed-purple flowers with darker eye and flowering over at least 10 weeks during the summer and fall.

1 Drawing Sheet

Botanical classification: *Hibiscus* hybrid (L.).
Variety denomination: 'Heartthrob'.

BACKGROUND AND ORIGIN OF THE PLANT

The present invention relates to the new and distinct hardy, herbaceous, *hibiscus* plant, *Hibiscus* 'Heartthrob' hybridized by Clarence H. Falstad, III in the summer of 2007 at a nursery in Zeeland, Mich. The new plant, originally labeled #F7-109-13, is from a cross between a proprietary hybrid 05-115-01 (not patented) (female, pod parent) times a proprietary red flowering selection of 'Southern Bell' (not patented) (male, pollen parent). Both parents have a complex mixture of species in them, most likely including at least the species: *moscheutos, coccineus. Hibiscus* 'Heartthrob' was first asexually propagated in 2010 by both stem cuttings and sterile tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Heartthrob' differs from its parents as well as all other hardy *hibiscus* known to the applicant in many traits. The most similar hardy herbaceous *hibiscus* know to the inventor is 'Robert Fleming' U.S. Plant Pat. No. 14,776. The flower of 'Heartthrob' is a darker richer red color than 'Robert Fleming' or either of the two parents, which had a brighter and lighter red flower. The plant habit of 'Heartthrob' is intermediate in size between the shorter female parent and the taller male parent and taller and less rounded in habit than 'Robert Fleming'. The foliage of 'Heartthrob' is generally ovate like both parents and 'Robert Fleming', but the apex of the leaves of the new plant are sharper and longer. There are many other hardy herbaceous *hibiscus* know to the inventor with red or reddish colored flowers including: 'Quatro Rojo' U.S. Plant Pat. No. 9,311, 'Fireball' U.S. Plant Pat. No. 13,631, 'My Valentine' U.S. Plant Pat. No. 24,108, 'Sultry Kiss' U.S. Plant Pat. No. 22,300, 'Midnight Marvel' U.S. Plant Pat. No. 24,079, 'Cranberry Crush' U.S. Plant Pat. No. 21,984 and 'Lord Baltimore' (not patented).

'Quatro Rojo' has dissected foliage and is also not as overlapping in flower petals as 'Heartthrob'. 'Fireball' is more open in habit and dissected leaves that 'Heartthrob' does not. The flowers of 'Cranberry Crush' are more cupped and it has foliage that is tri-lobed with purple tinting. 'Lord Baltimore' is taller in habit with lobed foliage. 'Sultry Kiss's is broader and less vertical in habit while also having lobed foliage. 'My Valentine' has lobed foliage, more cupped flowers and is shorter in habit than 'Heartthrob'.

*Hibiscus* 'Heartthrob' is a unique, hardy, herbaceous *hibiscus* with the following combined traits:

1. Hardy perennial with dense mostly upright branched stems.
2. Many large flat-faced flowers over an extended period.
3. Flower colors of dark, greyed-purple with an even darker blackish-red lustrous eye.
4. Broadly ovate-shaped, dark green foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
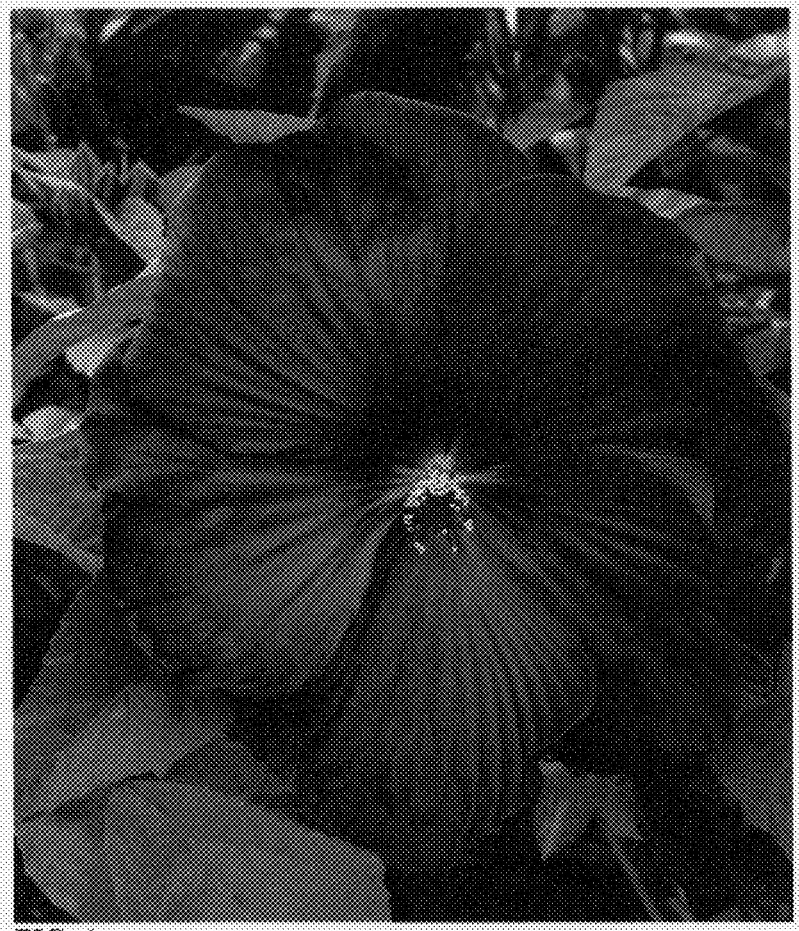
FIG. 1 shows a close-up of the dark, greyed-purple flowers with dark green foliage.
Figure 2:
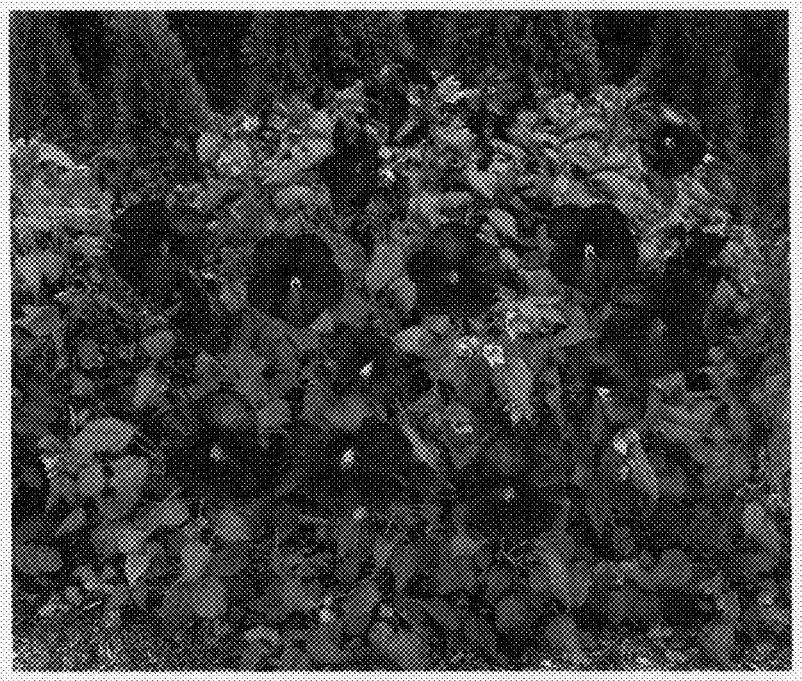
FIG. 2 shows the plant habit of a three year-old plant in full-sun.

The following descriptions and color references are based on the 2001 edition of The Royal Horticultural Society Colour Chart except where common dictionary terms are used. The new plant, *Hibiscus* 'Heartthrob', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand open field trials of a nursery in Zeeland, Mich. with supplemental fertilizer and water as needed. The plants are natural habit and were not treated with plant growth regulators, nor were they pinched at any time in the growth year.

Parentage: Proprietary hybrid 05-115-01(female, pod parent) times a proprietary red flowering selection of 'Southern Bell' (not patented) (male, pollen parent).

Propagation:

*Method*.—Stem cuttings and sterile plant tissue culture division.

*Time to initiate roots from tissue culture*.—About two weeks.

*Rooting habit*.—Normal, branching, fleshy, developing thick to about 3.5 cm diameter near base; root color greyed-orange between RHS 164D and lighter than RHS 159 D depending on soil type.

*Crop time*.—Under normal summer growing conditions 12 to 16 weeks to flower in a four-liter container from cutting. Plant vigor is very good.

Plant description:

*Plant shape and habit*.—Hardy herbaceous perennial with six thick upright and heavily branched main stems producing a rounded mound about 100.0 cm tall and 140.0 cm wide; about 15 to 25 stems per plant; 8 to 12 primary branches per main stem protruding upward at 45° to 60° angle from horizontal, secondary branches on about the lower one third of the primary branches; secondary branch size: between 8.0 cm and 30 cm long (shorter at the upper nodes) and average 1.0 cm diameter at the base of branch.

*Stem*.—Rounded, glabrous, glaucous; average 95.0 cm tall and 2.5 cm diameter at base.

*Stem color*.—Nearest RHS 138B with tinting of nearest RHS 155C in areas where the stem is getting more sun.

*Plant size*.—Unpinched plant with stems 100.0 cm tall; overall plant about 140.0 cm wide just above soil line (widest point).

*Internode*.—Shortest at top and longest in middle; about 28 nodes per stem, average internode length about 3.2 cm of unpinched plant, varied between 2.0 to 6.0 cm.

Foliage description: Alternate; crenate; glabrous; ovate to narrowly cordate with rounded to cordate bases and acute apexes; matte texture above and below; palmately veined; leaf blade size average 16 cm long and 10 cm wide, becoming smaller in distal portion of stem.

*Foliage color*.—Adaxial side between RHS 137A and RHS 139B; abaxial side nearest but more green than RHS 147B; leaf margins in strong direct sun may occasionally develop margins of nearest RHS 184A along the perimeter 1.0 to 2.0 mm.

*Veins*.—Palmate; primary and secondary adaxial veins developing tint nearest RHS 185B in areas of more direct sun exposure with a base color of more green than RHS 145C and more yellow than RHS 147D; primary and secondary abaxial veins more green than RHS 11D and more yellow than RHS 145D.

*Petioles*.—Average site 7.5 cm long and 4.0 mm wide; mostly cylindrical with proximal petioles more plano-convex; glaucous, glabrous.

*Petiole color*.—Above nearest RHS 146C with tinting between RHS 183D and RHS 182A concentrated in areas of more light; at base and where protected from light between RHS 138A and RHS 138B; below nearest RHS 144B along the center length with some tinting along the sides of nearest RHS 183D where still exposed to sun.

Flower description:

*Buds*.—One day prior to opening about 7.5 cm long and 3.5 cm in diameter, acute apex and bluntly rounded base, unopened petals wrinkled at veins, exposed petal color between RHS N186B and RHS N186C; prior to showing petals: buds are about 3.5 cm long and 2.5 cm in diameter, ovoid with acute apex, carinate at the fusion seam of the sepals; sepal color nearest RHS 138C with sepal carina nearest RHS N186C.

*Epicalyx*.—Entire, smooth, glabrous, linear with sharply acute apex and attenuate base, curved around sepals; 11 to 12 per flower; about 2.2 cm long tapering to base of about 2.5 mm wide; adaxial and abaxial color nearest RHS 146C.

*Sepals*.—Five, proximal half connate forming campanulate star-shaped calyx; acute apex; margin entire, edentate; individually about 4.2 cm long and 2.0 cm across, forming a corolla about 4.0 cm long and 5.0 cm diameter; adaxial color more yellow than RHS 147C, abaxial color darker green than RHS 144A; five primary sepal veins on abaxial surface same color as surrounding tissue and on adaxial surface between RHS 144D and RHS N144D.

*Flowers*.—16 to 22 per main stem without pinching; slightly cupped petals opening to about 170 degrees; upward and outwardly facing; about 23.0 cm across and 4.5 cm deep in center, larger in early part of flowering season; persist for a one to two days; effective for at least 10 weeks beginning mid-July and lasting into October; no detectable fragrance.

*Petals*.—Five; glabrous, slightly lustrous in center and matte in outer one half to two thirds on both adaxial and abaxial sides; adnate to the androecium, imbricate to about 90% overlapping at widest part (petals on either side overlapping above and below all but 10% of the petal in between); shape rounded; margins entire, edentate; apex rounded; base short claw-like; size: average 12.5 cm long and 13.5 cm wide at widest portion (larger in earlier part of flowering season); darker eye on front of about 6.0 cm across.

*Petal color*.—Adaxial between RHS 187A and RHS 187B; abaxial color nearest RHS 187A; petal veins ribbed on back and impressed on front producing a slightly ruffled appearance; vein color adaxial nearest RHS 187A on adaxial surface and the nearest RHS 187B and lustrous on abaxial surface; dark eye nearest RHS 187A.

*Gynoecium*.—Style: enclosed in column about 4.5 cm long and 8.0 mm wide at base; column color nearest RHS 59C at base and RHS 61B distally; style protruding from column 2.0 cm and split in distal 1.0 cm portion into five branches and protrudes from column, branch diameter 2.0 mm; style color before branch nearest RHS 59A and color after split between RHS 187B and RHS 187A; Stigma: five; globose, puberulose, about 2.0 mm in diameter, nearest RHS 187A; Ovary: superior, about 10.0 mm across at base and 8.0 mm tall; acute apex; color: closest to RHS 154D.

*Androecium*.—Filaments: numerous, about 120; less than 1.0 mm in diameter and about 5.0 mm long; attached to nearly the entire length of column; color between RHS 59C and RHS 59D at base and lightening just before anther to nearest RHS 65D; Anthers: reniform; about 2.0 mm long and 1.5 mm wide; nearest RHS 60C; Pollen: numerous, globose, less than 0.1 mm long, color nearest RHS 164C.

*Pedicel*.—Rounded, glabrous, from base of sepal to abscission point average 2.5 cm long and 3.0 mm wide on early flowers decreasing in distal flowers.

*Pedicel color*.—Base color nearest RHS 138B tinted nearest RHS 183B with high light exposure.

*Peduncle*.—rounded, glabrous, flowers are held easily visible on average 5.0 cm long from abscission point to stem and 3.0 mm wide, longer on earlier flowers; base color between RHS 138B and RHS 138A with a slight tinting of RHS 183B.

*Fruit*.—Few, loculicidal capsule; glabrous; globose, occasionally with abruptly acute apex; nearest RHS N199B when mature.

*Seed*.—Minutely floccose, globose to slightly reniform; about 3.0 mm in diameter; seed color nearest RHS 200A.

Disease and pest resistance: Resistance beyond that of other hardy *hibiscus* cultivars has not been observed. The plant grows and flowers best with plenty of moisture and adequate drainage, but is able to tolerate some drought when mature. Hardiness at least from USDA zone 4 through 9, and other disease resistance is typical of that of other hardy *hibiscus* cultivars.

I claim:

1. A new cultivar of hardy herbaceous *Hibiscus* hybrid plant named 'Heartthrob' as herein illustrated and described, comprising a hardy herbaceous perennial with dense mostly upright branched stems bearing broadly ovate-shaped dark green foliage and many large flat-faced, dark, greyed-purple flowers with darker eye suitable for landscape use.

* * * * *